US012797831B2

(12) United States Patent
Kado et al.

(10) Patent No.: US 12,797,831 B2
(45) Date of Patent: Nov. 17, 2026

(54) HYDROGENATION CATALYST, FLOW-TYPE ORGANIC SYNTHESIS SYSTEM USING THE SAME, AND MANUFACTURING METHOD OF HYDROGENATED ORGANIC COMPOUND

(71) Applicant: CHIYODA CORPORATION, Minatomirai (JP)

(72) Inventors: Shigeru Kado, Yokohama (JP); Toshiyuki Watanabe, Yokohama (JP); Asako Kiryu, Yokohama (JP)

(73) Assignee: CHIYODA CORPORATION, Minatomirai (JP)

( * ) Notice: Subject to any disclaimer, the term of this patent is extended or adjusted under 35 U.S.C. 154(b) by 493 days.

(21) Appl. No.: 18/555,886

(22) PCT Filed: Mar. 29, 2022

(86) PCT No.: PCT/JP2022/015479
§ 371 (c)(1),
(2) Date: Oct. 18, 2023

(87) PCT Pub. No.: WO2022/224741
PCT Pub. Date: Oct. 27, 2022

(65) Prior Publication Data
US 2024/0216893 A1 Jul. 4, 2024

(30) Foreign Application Priority Data
Apr. 21, 2021 (JP) ................................ 2021-072144

(51) Int. Cl.
*B01J 23/44* (2006.01)
*B01J 21/06* (2006.01)
*B01J 35/64* (2024.01)
*B01J 35/70* (2024.01)
*C07C 209/36* (2006.01)

(52) U.S. Cl.
CPC ............ *B01J 23/44* (2013.01); *B01J 21/063* (2013.01); *B01J 35/643* (2024.01); *B01J 35/647* (2024.01); *B01J 35/70* (2024.01); *C07C 209/365* (2013.01)

(58) Field of Classification Search
CPC ........ B01J 21/063; B01J 23/44; B01J 35/643; B01J 35/647; B01J 35/70; C07C 209/365
USPC ....... 502/339, 337, 333–335, 259, 262, 350; 568/942; 564/417, 418, 421, 422
See application file for complete search history.

(56) References Cited

U.S. PATENT DOCUMENTS

| | | | |
|---|---|---|---|
| 4,020,107 A | 4/1977 | Kosak | |
| 4,070,401 A | 1/1978 | Hirai et al. | |
| 4,760,187 A | 7/1988 | Kosak | |
| 5,387,726 A | 2/1995 | Bankmann et al. | |
| 6,140,539 A * | 10/2000 | Sander .................. | B01J 35/393 564/417 |
| 8,455,690 B2 | 6/2013 | Takenaka et al. | |
| 9,463,452 B2 | 10/2016 | Inoue et al. | |
| 9,776,180 B2 | 10/2017 | Inoue et al. | |
| 10,745,628 B2 | 8/2020 | Imagawa et al. | |
| 2011/0190115 A1 | 8/2011 | Ciriminna et al. | |

FOREIGN PATENT DOCUMENTS

| | | |
|---|---|---|
| JP | S51122029 A | 10/1976 |
| JP | S5235652 B2 | 9/1977 |
| JP | S5839646 A | 3/1983 |
| JP | H07133255 A | 5/1995 |
| JP | 2004277409 A | 10/2004 |
| JP | 4119144 B2 | 7/2008 |
| JP | 2011529780 A | 12/2011 |
| JP | 5599212 B2 | 10/2014 |
| JP | 2015188878 A | 11/2015 |
| JP | 6456204 B2 | 1/2019 |
| JP | 2020124663 A | 8/2020 |
| WO | 2008117844 A1 | 10/2008 |

OTHER PUBLICATIONS

English translation of Written Opinion for PCT/JP2022/015479. (Year: 2022).*
Sikhwivhilu, Lucky M. et al., "Selective hydrogenation of o-chloronitrobenzene over palladium supported nanotubular titanium dioxide derived catalysts," Catalysis Communications, No. 8 (2007), pp. 199-2006.
Xiong, Jun et al., Liquid-phase hydrogenation of o-chloronitrobenzene over supported nickel catalysts, Catalysis Communications, No. 8 (2007), pp. 345-350.
Coq, Bernard et al, "Influence of support and metallic precursor on the hydrogenation of p-chloronitrobenzene over supported platinum catalysts," Journal of Molecular Catalysis, No. 79 (1993); pp. 253-264.
International Search Report for Japanese Patent Application PCT/JP2022/015479 mailed Jun. 14, 2022; 3 pp.
Notification of first Office Action for Chinese Patent Application No. 202280029270.8 dated Sep. 27, 2025; 12 pp.
Extended European Search Report for European Patent Application No. 22791516.2, dated Mar. 19, 2025; 8 pp.

* cited by examiner

*Primary Examiner* — Patricia L. Hailey
(74) *Attorney, Agent, or Firm* — Armstrong Teasdale LLP

(57) ABSTRACT

A hydrogenation catalyst for hydrogenation of an aromatic halonitro compound includes: a carrier containing at least one of silica, titania, and alumina; and at least one metal carried by the carrier and selected from group 10 elements in a periodic table.

3 Claims, 10 Drawing Sheets

HYDROGENATION CATALYST, FLOW-TYPE ORGANIC SYNTHESIS SYSTEM USING THE SAME, AND MANUFACTURING METHOD OF HYDROGENATED ORGANIC COMPOUND

CROSS-REFERENCE TO RELATED APPLICATION

This application is a U.S. national stage application of PCT/JP2022/015479, filed on Mar. 29, 2022, which claims the benefit of priority to Japanese Patent Application No. 2021-072144, filed Apr. 21, 2021. The contents of these applications are hereby expressly incorporated by reference in their entirety.

TECHNICAL FIELD

The present invention relates to a hydrogenation catalyst for a hydrogenation reaction of an aromatic halonitro compound, a flow-type organic synthesis system using the hydrogenation catalyst, and a manufacturing method of a hydrogenated organic compound.

BACKGROUND ART

In the hydrogenation to add hydrogen to an unsaturated bond of an aromatic halonitro compound, a dehalogenation reaction (separation of halogen) easily occurs, which lowers the yield and quality of a halogenated aromatic amine as a target product.

Conventionally, as a technique for suppressing the dehalogenation reaction in the hydrogenation of the aromatic halonitro compound, a method of causing hydrogen reduction of the aromatic halonitro compound in the presence of an acidic phosphorus compound is known, for example (see Patent Document 1). Further, a method of hydrogenating the aromatic halonitro compound by using an organic nitrogen base (alkylamines, alicyclic amines, or guanidine) is known (see Patent Document 2). Further, a method of causing halogenated benzenes to coexist and producing halogenated anilines from halogenated nitrobenzenes by contact reduction is known (see Patent Document 3). Further, a method of hydrogenating the aromatic halonitro compound by using a hydrogenation catalyst in the presence of carbon dioxide is known (see Patent Document 4).

PRIOR ART DOCUMENT(S)

Patent Document(s)

Patent Document 1: JPS51-122029A
Patent Document 2: JPS52-35652B
Patent Document 3: JPH7-133255A
Patent Document 4: JP2004-277409A

SUMMARY OF THE INVENTION

Task to be Accomplished by the Invention

In a case where additives, gases, or the like (hereinafter referred to as "dehalogenation inhibitor") is used for suppressing the dehalogenation reaction like the conventional techniques described in Patent Documents 1 to 4, the recovery process of the dehalogenation inhibitor is required. Accordingly, the manufacturing process of a product (target product) becomes complicated, and there is a risk that the dehalogenation inhibitor is mixed into the product. Furthermore, the conventional technique described in Patent Document 4 increases the load of safety control and product quality control in the manufacturing process that handles carbon dioxide.

Further, in the hydrogenation of the aromatic halonitro compound (for example, halonitrobenzene), a nitroso compound (for example, nitrosobenzene) may be produced as a by-product. Since the nitroso compound is harmful to humans, aquatic creatures, and the like and can burn explosively, it is particularly important to suppress the production of the nitroso compound.

The present invention is made in view of such problems of conventional techniques, and a main purpose thereof is to provide a hydrogenation catalyst, a flow-type organic synthesis system using the same, and a manufacturing method of a hydrogenated organic compound that can improve, in the hydrogenation of an aromatic halonitro compound, the yield of halogenated aromatic amine as a target product without the need for a dehalogenation inhibitor while suppressing the production of a nitroso compound.

Means to Accomplish the Task

In the first aspect of the present invention, a hydrogenation catalyst for hydrogenation of an aromatic halonitro compound comprises: a carrier containing at least one of silica, titania, and alumina; and at least one metal carried by the carrier and selected from group 10 elements in a periodic table.

Accordingly, it is possible to improve, in the hydrogenation of an aromatic halonitro compound, the yield of halogenated aromatic amine as a target product without the need for a dehalogenation inhibitor while suppressing the production of a nitroso compound.

In the second aspect of the present invention, the metal is palladium.

Accordingly, it is possible to effectively improve, in the hydrogenation of an aromatic halonitro compound, the yield of halogenated aromatic amine as a target product while effectively suppressing the production of a nitroso compound.

In the third aspect of the present invention, the carrier is a composite carrier composed of alumina and titania, and the composite carrier includes a structure that a base material made of alumina is coated with titania.

Accordingly, it is possible to effectively improve, in the hydrogenation of an aromatic halonitro compound, the yield of halogenated aromatic amine as a target product while effectively suppressing the production of a nitroso compound.

In the fourth aspect of the present invention, the carrier contains titania that includes, as a crystal structure, 38% or more of an anatase-type.

Accordingly, in a case where a hydrogenation catalyst with a carrier containing titania is used in the hydrogenation of an aromatic halonitro compound, it is possible to effectively improve the yield of halogenated aromatic amine as a target product while effectively suppressing the production of a nitroso compound.

In the fifth aspect of the present invention, the carrier containing titania does not include, as the crystal structure, a rutile-type.

Accordingly, in a case where a hydrogenation catalyst with a carrier containing titania is used in the hydrogenation of an aromatic halonitro compound, it is possible to more effectively improve the yield of halogenated aromatic amine as a target product while more effectively suppressing the production of a nitroso compound.

In the sixth aspect of the present invention, an average pore diameter of the carrier containing titania is 78 times or less of a longitudinal molecular length of the aromatic halonitro compound.

Accordingly, it is possible to effectively improve, in the hydrogenation of an aromatic halonitro compound, the yield of halogenated aromatic amine as a target product while effectively suppressing the production of a nitroso compound.

In the seventh aspect of the present invention, an average pore diameter of the carrier is approximately 50 nm or less.

Accordingly, it is possible to effectively improve, in the hydrogenation of an aromatic halonitro compound, the yield of halogenated aromatic amine as a target product while effectively suppressing the production of a nitroso compound.

In the eighth aspect of the present invention, a flow-type organic synthesis system is configured to cause a gas/liquid/solid three phase reaction by using: a fixed catalyst including the hydrogenation catalyst according to any one of the first to seventh aspects; hydrogen as a gas raw material; and the aromatic halonitro compound as a liquid raw material.

Accordingly, it is possible to more precisely control the reaction temperature as compared with a batch method. Accordingly, it is possible to improve the yield of halogenated aromatic amine as a target product without the need for a dehalogenation inhibitor while suppressing the production of a nitroso compound. Further, the recovery process of the hydrogenation catalyst after the reaction in the batch method becomes unnecessary, and there is an advantage that the scale can be more easily increased as compared with the batch method.

In the ninth aspect of the present invention, a manufacturing method of a hydrogenated organic compound hydrogenates the aromatic halonitro compound by using the hydrogenation catalyst according to any one of the first to seventh aspects.

Accordingly, it is possible to improve, in the hydrogenation of an aromatic halonitro compound, the yield of halogenated aromatic amine as a target product without the need for a dehalogenation inhibitor while suppressing the production of a nitroso compound.

Effect of the Invention

Thus, according to the present invention, it is possible to improve, in the hydrogenation of an aromatic halonitro compound, the yield of halogenated aromatic amine as a target product without the need for a dehalogenation inhibitor while suppressing the production of a nitroso compound.

BRIEF DESCRIPTION OF THE DRAWING(S)

DETAILED DESCRIPTION OF THE INVENTION

Figure 1:
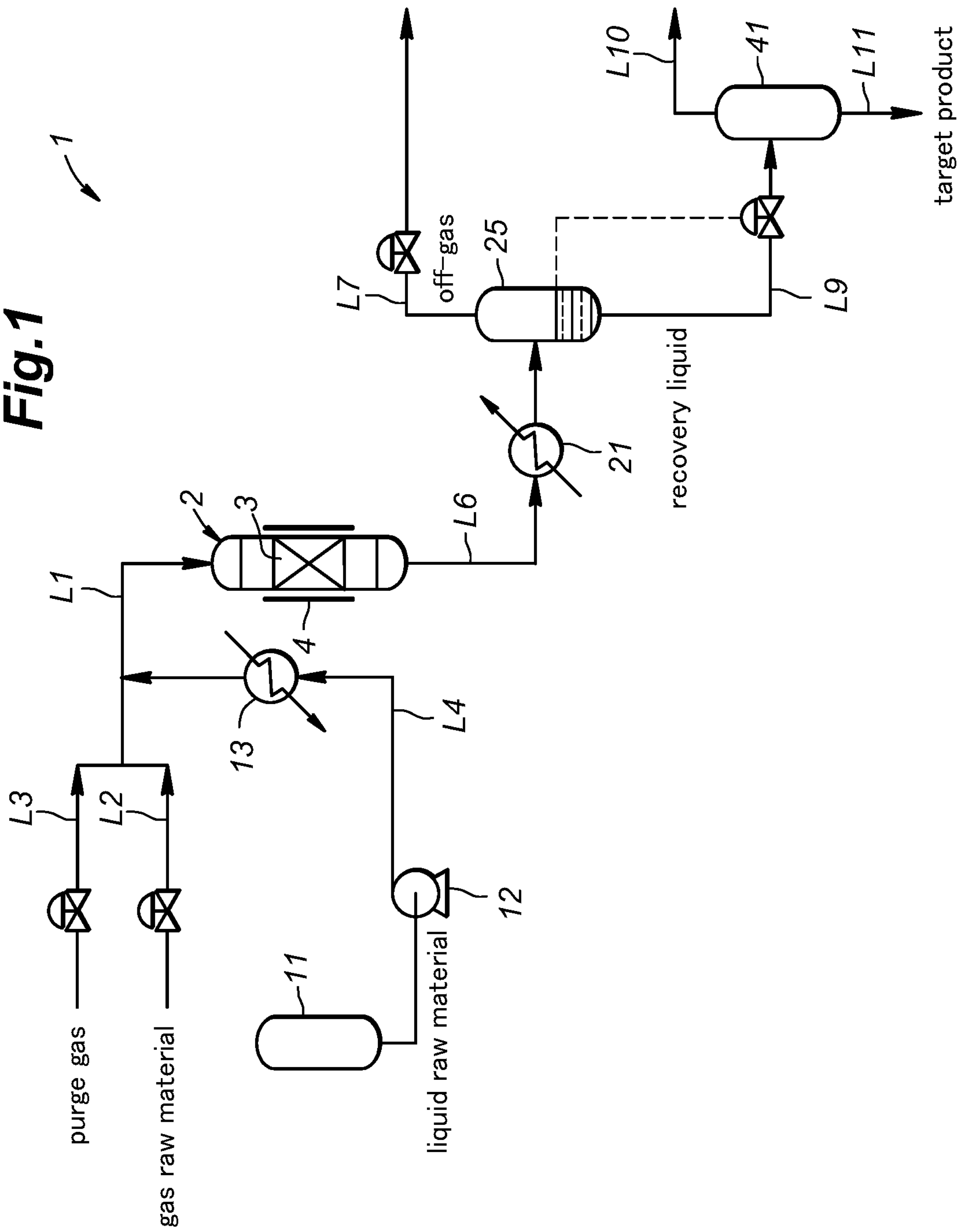
FIG. 1 is a diagram showing an overall configuration of a flow-type organic synthesis system for the hydrogenation of an aromatic halonitro compound according to an embodiment.

In the following, with reference to the drawings, a hydrogenation catalyst, a flow-type organic synthesis system using the hydrogenation catalyst, and a manufacturing method of a hydrogenated organic compound according to an embodiment will be described.

(Hydrogenation Catalyst)

The hydrogenation catalyst according to the present embodiment has a structure that at least one metal (hereinafter referred to as "catalytic metal") selected from group 10 elements in a periodic table is carried by a carrier containing at least one of silica ($SiO_2$), titania ($TiO_2$), and alumina ($Al_2O_3$).

This hydrogenation catalyst is especially used for the hydrogenation of an aromatic halonitro compound, thereby causing a unique effect that has not been caused by conventional catalysts used for the hydrogenation of the aromatic halonitro compound. More specifically, the hydrogenation catalyst can improve, in the hydrogenation of the aromatic halonitro compound, the yield of halogenated aromatic amine (hydrogenated organic compound) as a target product without the need for a dehalogenation inhibitor while suppressing the production of a nitroso compound as a by-product.

As the catalytic metal, nickel (Ni), palladium (Pd), platinum (Pt), or the like included in the group 10 elements in the periodic table can be used, and palladium is particularly preferable. A palladium precursor is not limited, and a nitrate, a sulfate, a chloride, an acetylacetone complex, or the like can be used as a palladium compound, for example. The catalytic metal is dispersed and carried on an outer surface of the carrier and inner surfaces of pores of the carrier.

The shape and size (average particle size or the like) of a base material such as silica, titania, and alumina contained in the carrier are not limited, and various shapes and sizes can be adopted depending on the specification of a reactor used in a hydrogenation reaction of the aromatic halonitro compound, reaction conditions, and the like. As the base material composed of at least one of silica, titania, and alumina, a commercially available base material for a catalytic carrier can be used. As an example of commercially available silica for a catalytic carrier, the CARiACT Q series manufactured by Fuji Silysia Chemical Ltd. can be given. Further, as an example of commercially available titania for a catalytic carrier, the CS-300S-12 series and CS-950-12 series manufactured by Sakai Chemical Industry Co., Ltd. can be given. Further, as an example of commercially available alumina for a catalytic carrier, the neobead GB series manufactured by Mizusawa Industrial Chemicals, Ltd. can be given.

Further, as the base material containing at least one of silica, titania, and alumina, a material (porous inorganic oxide), which is obtained by synthesizing a hydrosol or hydrogel of a metal hydrous oxide by pH swing, can be used. The pH swing alternately swings the hydrosol or hydrogel of the metal hydrous oxide plural times between a precipitation pH region and a dissolution pH region thereof.

The metal hydrous oxide is a hydrous oxide of one or more metals selected from silicon (Si), titanium (Ti), and aluminum (Al). For a metal compound used as a raw material for synthesizing the hydrosol or hydrogel of the metal hydrous oxide, for example, a chloride, a fluoride, a bromide, and an iodide thereof, salts such as nitrate, sulfate, carbonate, acetate, phosphate, borate, oxalate, hydrofluoric acid salt, silicate, and iodate, oxoacid salt, alkoxides, and the like can be used. Only one kind of metal compound may be used singly, or plural kinds of metal compound may be used as a mixture.

As a silicon compound, for example, colloidal silica ($SiO_2 \cdot XH_2O$), ultrafine anhydrous silica ($SiO_2$), Sodium Silicate [$Na_2O \cdot XSiO_2 \cdot YH_2O$ (X is in the range of 1 to 4)], Silicon Tetrachloride ($SiCl_4$), Silicate Ester [$Si(OCH_3)_4$, $Si(OC_2H_5)_4$], or the like can be used.

As a titanium compound, for example, titanium tetrachloride ($TiCl_4$), Titanium sulfate [$Ti_2(SO_4)_3$, $Ti(SO_4)_2$], titanium oxysulfate ($TiOSO_4$), titanium trichloride ($TiCl_3$), titanium bromide ($TiBr_4$), titanium fluoride ($TiF_4$, $TiF_3$), titanium oxide ($TiO_2$), orthotitanic acid ($H_4TiO_4$), metatitanic acid ($H_2TiO_3$), titanium methoxide [$Ti(OCH_3)_4$], titanium ethoxide [$Ti(OC_2H_5)_4$], titanium propoxide [$Ti(OC_3H_7)_4$], titanium isopropoxide {$Ti[OCH(CH_3)_2]_4$}, titanium butoxide [$Ti(OC_4H_9)_4$], or the like can be used.

As an aluminum compound, for example, metal aluminum (Al), aluminum chloride ($AlCl_3$, $AlCl_3 \cdot 6H_2O$), aluminum nitrate [$Al(NO_3)_3 \cdot 9H_2O$], aluminum sulfate [$Al_2(SO_4)_3$, $Al_2(SO_4)_3 \cdot 18H_2O$], polyaluminum chloride [$(Al_2(OH)_n Cl_{6-n})_m$ ($1<n<5$, $m<10$)], ammonium alum [$NH_4Al(SO_4)_2 \cdot 12H_2O$], sodium aluminate ($NaAlO_2$), potassium aluminate ($KAlO_2$), aluminum isopropoxide [$Al[OCH(CH_3)_2]_3$], aluminum ethoxide [$Al(OC_2H_5)_3$], aluminum-t-butoxide [$Al[OC(CH_3)_3]_3$], aluminum hydroxide [$Al(OH)_3$], or the like can be used.

For details of such a carrier synthesized by pH swing and its manufacturing method, see porous inorganic oxide and its manufacturing method disclosed in Japanese Patent No. 4119144, for example. The disclosed contents of this incorporated document constitute a portion of this specification, and the detailed description thereof will be omitted. Using such a carrier synthesized by pH swing, (the average or distribution of) the pore diameter of the catalyst can be controlled at a desired value by pH swing. Further, it is possible to finely adjust the value of the pore diameter by adjusting a calcination temperature of the carrier at the time of calcination.

Further, as the carrier, a composite carrier composed of alumina and titania may be used. The composite carrier includes a structure that a base material made of alumina is coated with titania. As the shape of the composite carrier, for example, a skeleton structure can be used. In the skeletal structure, a large number of pores are formed, as a plurality of needle-like or columnar structures is three-dimensionally intertwined. Such a structure can increase the specific surface area (a ratio of a pore volume to a pore diameter) of the hydrogenation catalyst and facilitate control of the pore structure.

For details of such a composite carrier, see the carrier and its manufacturing method disclosed in Japanese Patent No. 6456204, for example. The disclosed contents of this incorporated document constitute a portion of this specification, and the detailed description thereof will be omitted. Using the composite carrier, it is possible to realize, with a relatively small amount of the catalytic metal, a catalyst that excels in stability and suppression of side reactions.

The carrier containing titania preferably contains titania including, as a crystal phase (crystal structure), 38% or more of an anatase-type. Accordingly, it is possible to stably improve the yield of halogenated aromatic amine as a target product while effectively suppressing the production of the nitroso compound. Further, the carrier more preferably contains titania including, as the crystal phase, 96% or more of the anatase-type, and more preferably contains titania including 100% of the anatase-type. The proportion of the anatase-type in the crystal phase can be changed by changing the calcination temperature of the carrier. In particular, the carrier containing titania preferably includes, as the crystal phase, 38% or more of the anatase-type, and does not include, as the crystal phase, a rutile-type. Further, the crystal phase of the carrier can be confirmed by X-ray diffraction analysis using an X-ray diffraction device.

The average pore diameter of the carrier containing at least one of silica and titania is preferably approximately 50 nm or less. Accordingly, it is possible to stably improve the yield of halogenated aromatic amine as a target product while effectively suppressing the production of the nitroso compound. Further, the average pore diameter of the carrier containing titania is more preferably approximately 18 nm or less, and more preferably approximately 7 nm or less.

Further, the average pore diameter of the carrier containing silica is preferably 75 times or less of a longitudinal molecular length of the aromatic halonitro compound. Accordingly, it is possible to stably improve the yield of the halogenated aromatic amine as a target product while effectively suppressing the production of the nitroso compound. Further, the average pore diameter of the carrier containing titania is preferably 78 times or less of the longitudinal molecular length of the aromatic halonitro compound. The average pore diameter of the carrier containing titania is more preferably 28 times or less of the longitudinal molecular length of the aromatic halonitro compound, and more preferably 11 times or less thereof.

The average pore diameter of the carrier can be measured using a pore distribution measuring device (for example, a mercury porosimeter). Further, the longitudinal molecular length of the aromatic halonitro compound can be calculated using a quantum chemical calculation program.

For the production of the abovementioned hydrogenation catalyst that causes the carrier to carry the catalytic metal, the processes described in the above-mentioned documents and known catalyst production processes (for example, an impregnation process, a drying process, a calcination process, a reduction process, or the like) can be appropriately used. Further, the catalyst (or the carrier) can be formed into a desired shape such as a spherical shape, a columnar shape, a cylindrical shape, or the like depending on the purpose of use. Further, the size (particle size or the like) of the catalyst (or the carrier) can be set appropriately.

(Hydrogenation of the Aromatic Halonitro Compound)

Next, the hydrogenation reaction of the aromatic halonitro compound using the hydrogenation catalyst according to the present embodiment will be described.

The hydrogenation of the aromatic halonitro compound is represented by the following general Formula (1).

[Formula (1)]

(1)

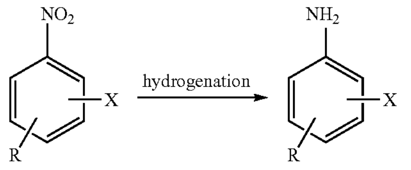

In Formula (1), "X" represents fluorine, chlorine, bromine, or iodine. Further, "R" represents a hydrogen atom, a hydroxyl group, a carboxyl group, a sulfo group, an alkyl group, an alkenyl group, an aralkyl group, an aryl group, an acyl group, an aroyl group, an alkoxy group, or an alkoxycarbonyl group.

In the following, as the hydrogenation of the aromatic halonitro compound, the hydrogenation of 4-chloronitrobenzene will be described as an example. In the hydrogenation of 4-chloronitrobenzene, as shown in the process of Formula (2), as hydrogen is added to 4-chloronitrobenzene as a raw material, 4-chloroaniline as a target product is produced via 4-chloronitrosobenzene and 4-chlorophenylhydroxylamine as intermediates. Finally, 4-chloroaniline is reduced to aniline. On the other hand, according to dehalogenation of 4-chloronitrobenzene, nitrobenzene may be produced. According to hydrogenation of nitrobenzene, aniline is produced via nitrosobenzene and hydroxylamine as intermediates. In the hydrogenation reaction in the present embodiment, only 4-chloronitrosobenzene is detected as an intermediate, and the detection of nitrosobenzene is negligible.

[Formula 2]

(2)

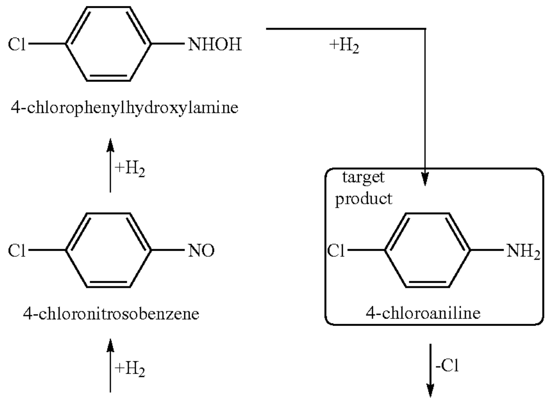

-continued

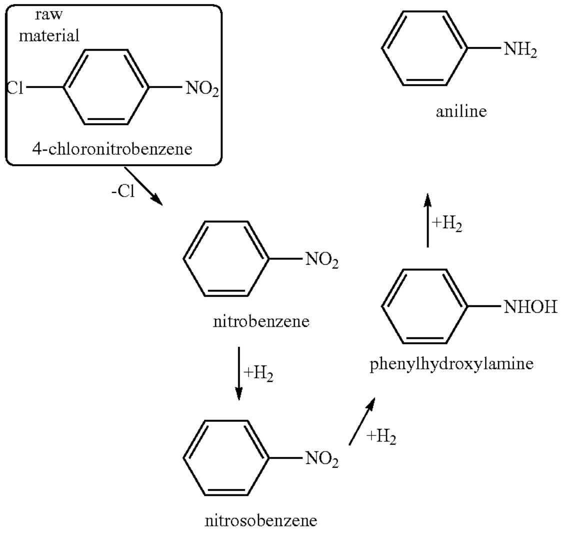

4-chloronitrobenzene may be hydrogenated using any of a batch type, a semi-batch type, and a flow-type, and the hydrogenation catalyst according to the present embodiment is particularly suitable as a flow-type reaction catalyst used in a flow-type reaction system that causes a gas/liquid/solid three phase reaction.

Next, with reference to FIG. 1, an example of the configuration of the flow-type organic synthesis system 1 (hydrogenation reaction system) will be described.

The flow-type organic synthesis system 1 includes a flow-type fixed bed reactor 2 (hereinafter referred to as "reactor 2") that causes the gas/liquid/solid three phase reaction by using hydrogen as a gas raw material, 4-chloronitrobenzene as a liquid raw material, and the hydrogenation catalyst as a solid catalyst. For the liquid raw material, an organic solvent (alcohol, ether, other aromatic hydrocarbons, or the like) inert to the reaction can be used. In a case where the aromatic halonitro compound to be hydrogenated is liquid, the reaction can be caused without a solvent.

The reactor 2 is a known tubular reactor accommodating a catalyst layer 3 including the hydrogenation catalyst. The reactor 2 causes a reaction by causing the gas raw material and the liquid raw material, which are continuously supplied from an inlet line L1, to flow into the catalyst layer 3. Further, the reactor 2 is provided with a tubular electric furnace 4 composed of two independent blocks, and can adjust the reaction temperature (more specifically, the temperature of the catalyst layer 3) by supplying heat as required. As the reactor 2, for example, it is possible to use not only a down-flow reactor that causes the raw materials to flow in the same direction as gravity but also an up-flow reactor that causes the raw materials to flow in the opposite direction to gravity.

The gas raw material is continuously supplied to the reactor 2 via a gas raw material supply line L2 connected to the inlet line L1. Further, the inlet line L1 is connected to a purge gas supply line L3 through which a purge gas flows. In the flow-type organic synthesis system 1, it is possible to perform a purging operation of equipment, piping, or the like inside the system by supplying the purge gas to the purge gas supply line L3 at the time of maintenance or the like.

The liquid raw material is stored in a liquid raw material tank 11. A liquid raw material pump 12 causes the liquid raw material to flow into the inlet line L1 via a liquid raw material supply line LA, and the liquid raw material is continuously supplied to the reactor 2 together with the gas raw material. Further, the liquid raw material supply line LA is provided with a preheater/precooler 13. The preheater/precooler 13 heats or cools the liquid raw material, thereby adjusting the temperature of the liquid raw material supplied to the reactor 2 within a preset target range.

Further, from the reactor 2, a reaction product mainly containing 4-chloroaniline is continuously discharged to an outlet line L6. The outlet line L6 is provided with a heat exchanger 21. The heat exchanger 21 heats or cools the reaction product, thereby controlling the temperature of the reaction product discharged from the reactor 2 within a preset target range.

The reaction product cooled by the heat exchanger 21 is supplied to a main drum 25 (gas-liquid separator) connected to a downstream portion of the outlet line L6. In the main drum 25, the reaction product is gas-liquid separated into an off-gas (residual gas) containing an unreacted gas raw material and the like and a recovery liquid containing a target (product) of the reaction.

The off-gas (gas phase component) separated in the main drum 25 is discharged via an off-gas transportation line L7 (the first line of a residual gas transportation line).

The recovery liquid from the main drum 25 is supplied to a product recovery drum 41 via a recovery liquid transportation line L9 (target recovery line). In the product recovery drum 41, the gas remaining in the recovery liquid is gas-liquid separated from the recovery liquid. This separated gas is discharged to the outside via a separated gas discharge line L10. Further, the recovery liquid (target product) separated in the product recovery drum 41 is recovered via a product recovery line L11.

In the flow-type organic synthesis system 1, an operator appropriately samples the recovery liquid from the product recovery line L11 at prescribed timings. The operator can identify and quantify 4-chloroaniline or the like as a target product (product) by analyzing the recovery liquid using liquid chromatograph or gas chromatograph.

EXAMPLES

In the flow-type organic synthesis system 1 (see FIG. 1), an experiment was conducted to produce 4-chloroaniline (hereinafter referred to as "4-CIAN") as a target product by hydrogenating 4-chloronitrobenzene (hereinafter referred to as "4-CINB") using each of the following catalysts A to G as a hydrogenation catalyst.

In the present embodiment, a commercially available Pd/C (palladium carbon) catalyst ("5% Palladium on Activated Carbon, Degussa type E 106 R/W 5% Pd (wetted with ca.55% water)" manufactured by Wako Pure Chemical Industries, Ltd.) carrying 5 wt. % of metal was used as a catalyst (hereinafter referred to as "Pd/C catalyst") to be compared with the hydrogenation catalyst.

(Catalyst A)

A commercially available silica gel ("CARIACT Q-10" manufactured by Fuji Silysia Chemical Ltd.) for a catalytic carrier was calcined at 500° C. for 3 hours, and weighed to be 5 g. Subsequently, the calcined silica gel was impregnated with a 0.42% palladium nitrate aqueous solution [$Pd(NO_3)$ aq] such that Pd is carried at 2 wt. %, and calcined at 500° C. for 3 hours after being dried. Accordingly, the catalyst A (Pd-carried silica catalyst) was acquired.

(Catalyst B)

A commercially available silica gel ("CARiACT Q-50" manufactured by Fuji Silysia Chemical Ltd.) for a catalytic carrier was calcined at 500° C. for 3 hours, and weighed to be 5 g. Subsequently, the calcined silica gel was impregnated with a 0.42% palladium nitrate aqueous solution [$Pd(NO_3)$ aq] such that Pd is carried at 2 wt. %, and calcined at 500° C. for 3 hours after being dried. Accordingly, the catalyst B (Pd-carried silica catalyst) was acquired.

(Catalyst C)

A titania carrier prepared by pH swing was calcined at 500° C. for 3 hours, and weighed to be 5 g. Subsequently, the calcined titania carrier was impregnated with a 0.42% palladium nitrate aqueous solution [$Pd(NO_3)$aq] such that Pd is carried at 2 wt. %, and calcined at 500° C. for 3 hours after being dried. Accordingly, the catalyst C (Pd-carried titania catalyst) was acquired. The titania carrier prepared by pH swing was manufactured by a known method similar to the manufacturing method of a titania carrier disclosed in Japanese Patent No. 5599212 (see [0123]).

(Catalyst D)

A commercially available titania ("CS-300S-12" manufactured by Sakai Chemical Industry Co., Ltd.) for a catalytic carrier was calcined at 500° C. for 3 hours, and weighed to be 5 g. Subsequently, the calcined titania was impregnated with a 0.42% palladium nitrate aqueous solution [$Pd(NO_3)$ aq] such that Pd is carried at 2 wt. %. and calcined at 500° C. for 3 hours after being dried. Accordingly, the catalyst D (Pd-carried titania catalyst) was acquired. The catalyst D includes not only a catalyst with a carrier calcined at 500° C. but also a catalyst with a carrier calcined at other temperatures (600° C., 700° C., 800° C., 900° ° C., and 950° C.).

(Catalyst E)

A commercially available titania ("CS-950-12" manufactured by Sakai Chemical Industry Co., Ltd.) for a catalytic carrier was calcined at 500° C. for 3 hours, and weighed to be 5 g. Subsequently, the calcined titania was impregnated with a 0.42% palladium nitrate aqueous solution [$Pd(NO_3)$ aq] such that Pd is carried at 2 wt. %. and calcined at 500° C. for 3 hours after being dried. Accordingly, the catalyst E (Pd-carried titania catalyst) was acquired.

(Catalyst F)

An alumina carrier prepared by pH swing was calcined at 500° C. for 3 hours, and weighed to be 5 g. Subsequently, the calcined alumina carrier was impregnated with a 0.42% palladium nitrate aqueous solution [$Pd(NO_3)$aq] such that Pd is carried at 2 wt. %, and calcined at 500° ° C. for 3 hours after being dried. Accordingly, the catalyst F (Pd-carried alumina catalyst) was acquired. The alumina carrier prepared by pH swing was manufactured by a known method similar to the manufacturing method of an alumina carrier disclosed in Japanese Patent No. 5599212 (see AS-2).

(Catalyst G)

A titania-coating alumina carrier (HBT) prepared by pH swing was calcined at 500° C. for 3 hours, and weighed to be 5 g. Subsequently, the calcined titania-coating alumina carrier was impregnated with a 0.42% palladium nitrate aqueous solution [$Pd(NO_3)$aq] such that Pd is carried at 2 wt. %, and calcined at 500° C. for 3 hours after being dried. Accordingly, the catalyst G (Pd-carried titania-coating alumina catalyst) was acquired. The titania-coating alumina carrier (HBT) prepared by pH swing was manufactured by a known method similar to the manufacturing method of a titania-coating alumina carrier disclosed in Japanese Patent No. 5599212 (see AT-2).

In the hydrogenation reaction of 4-chloronitrobenzene using the flow-type organic synthesis system 1, the center of the catalyst layer 3 was arranged on a second stage (upper stage) of the tubular electric furnace 4 composed of two independent blocks, after a stainless steel reactor tube of the reactor 2 is filled with 1.0 g of the hydrogenation catalyst. Then, the catalyst layer 3 was heated such that the temperature at the center thereof was 40° ° C. Subsequently, using the liquid raw material pump 12, 4-CINB/TOL-IPA (toluene isopropyl alcohol solvent) as a liquid raw material was supplied to the reaction tube at a flow rate of 0.2 ml/min, and hydrogen as a gas raw material was supplied to the reaction tube at a flow rate of 20 $cm^3$/min. With the initiation of the hydrogenation reaction (reduction reaction) of the liquid raw material, the temperature of the hydrogenation catalyst increases according to the heat generated by the liquid raw material. Accordingly, by adjusting the temperature of each block of the electric furnace 4 during the reaction, the temperature at the center of the catalyst layer 3 during the reaction was controlled at 40° C. After the reaction, the product was cooled, recovered, and analyzed by gas chromatography. Further, the flow rate of an outflow gas after cooling the product was measured by a mass flowmeter. From the analysis and measurement results, the conversion of 4-CINB, the selectivity of 4-CIAN (target product), and the selectivity of 4-chloronitrosobenzene (nitroso compound) were calculated. Such an experiment on the hydrogenation reaction of 4-chloronitrobenzene was conducted for each of the hydrogenation catalysts (the catalysts A to G) and the Pd/C catalyst.

Figure 2:
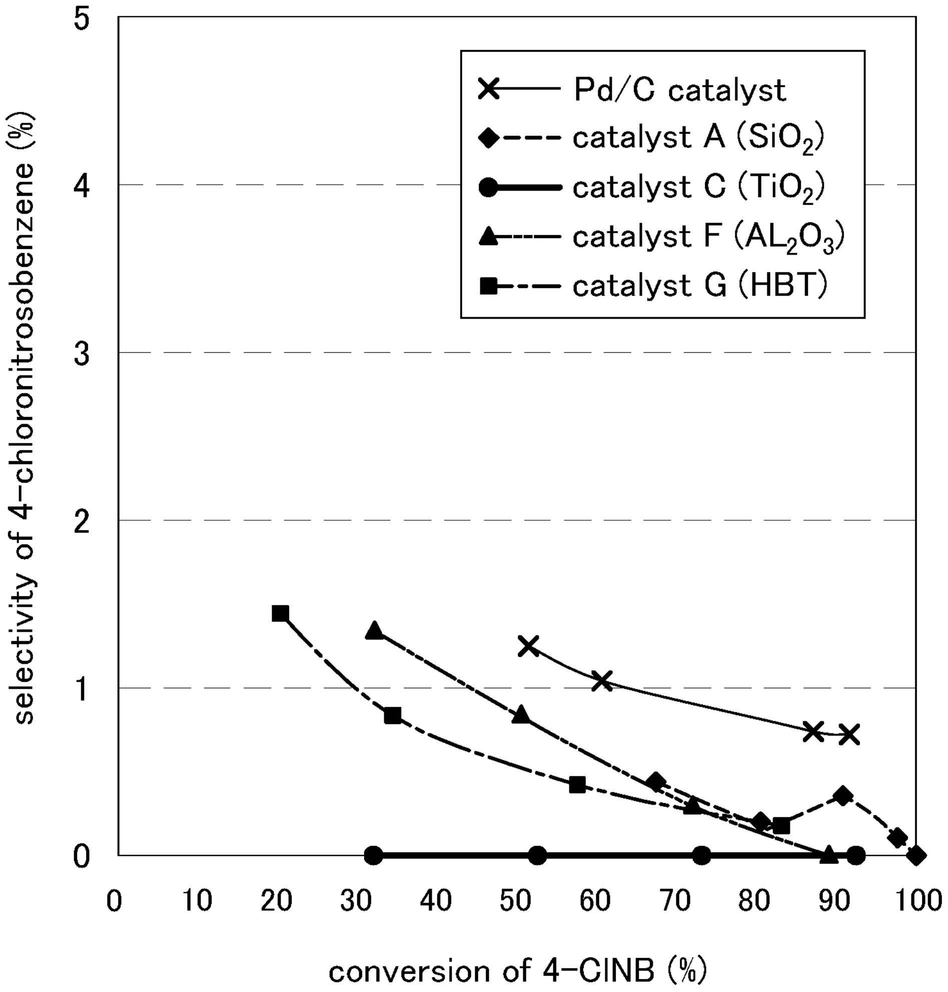
FIG. 2 is a graph (for a catalyst A, a catalyst C, a catalyst F, and a catalyst G) showing the relationship between the conversion of 4-CINB and the selectivity of a nitroso compound in the hydrogenation reaction.
Figure 3:
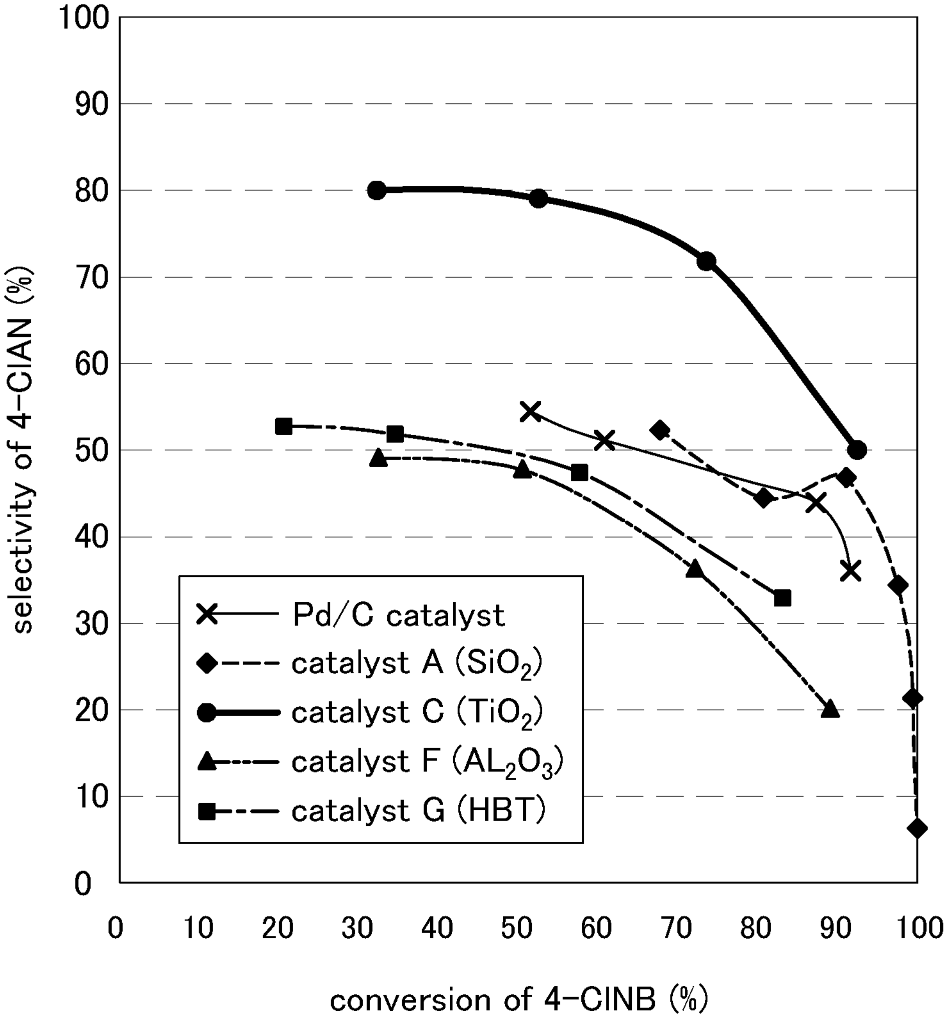
FIG. 3 is a graph (for the catalyst A, the catalyst C, the catalyst F, and the catalyst G) showing the relationship between the conversion of 4-CINB and the selectivity of 4-CIAN in the hydrogenation reaction.

FIG. 2 is a graph showing the relationship between the conversion of 4-CINB as a liquid raw material and the selectivity of the nitroso compound (more specifically, 4-chloronitrosobenzene) in the hydrogenation reaction for the catalyst A, the catalyst C, the catalyst F, the catalyst G, and the Pd/C catalyst (comparative catalyst). FIG. 3 is a graph showing the relationship between the conversion of 4-CINB as a liquid raw material and the selectivity of 4-CIAN in the hydrogenation reaction for the same catalysts as in FIG. 2.

In FIG. 2, it is confirmed that the selectivity of the nitroso compound for all of the catalyst A, the catalyst C, the catalyst F, and the catalyst G is lower than the selectivity of the nitroso compound for the Pd/C catalyst in a case where the conversion of 4-CINB is a similar value. In particular, when the catalyst C containing titania is used, the nitroso compound is hardly produced.

In FIG. 3, it is confirmed that the selectivity of 4-CIAN for the catalyst C is higher than the selectivity of 4-CIAN for the Pd/C catalyst in a case where the conversion of 4-CINB is a similar value. Further, it is confirmed that the selectivity of 4-CIAN for the catalyst A is approximately equal to or higher than the selectivity of 4-CIAN for the Pd/C catalyst, although the selectivity of 4-CIAN for the catalyst A is slightly lower than the selectivity of 4-CIAN for the Pd/C catalyst in a portion (approximately 80%) of the conversion of 4-CINB.

Figure 4:
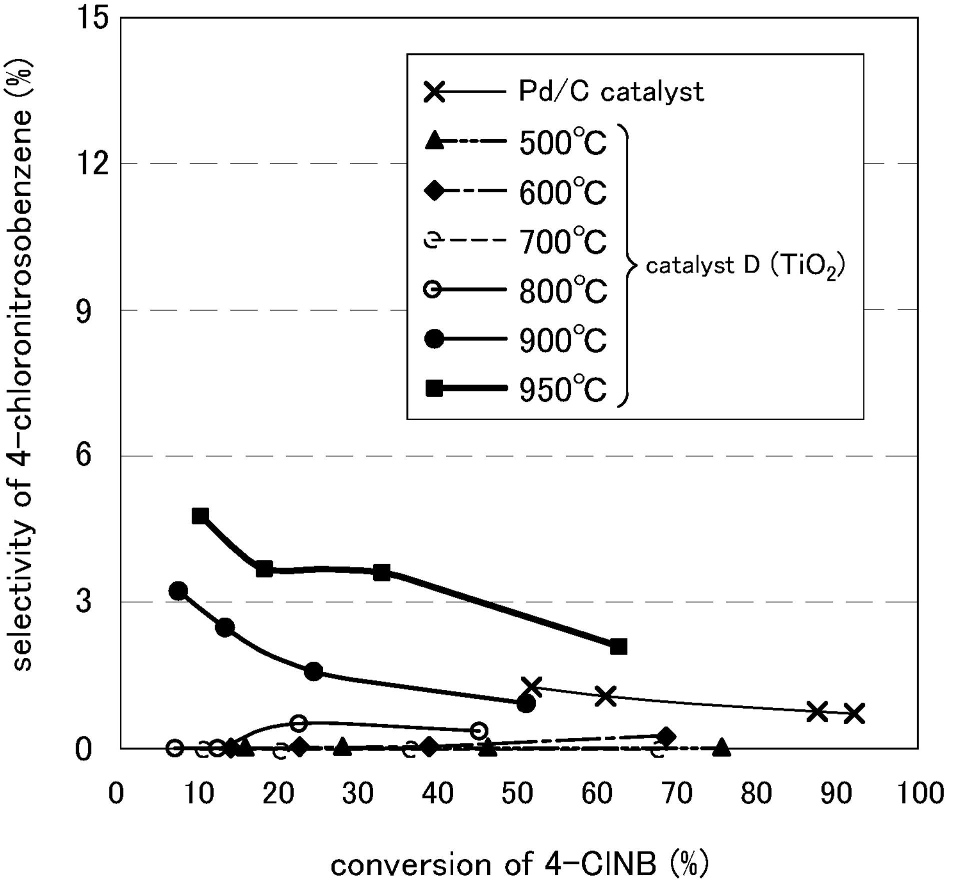
FIG. 4 is a graph (for a catalyst D) showing the relationship between the conversion of 4-CINB and the selectivity of the nitroso compound in the hydrogenation reaction.
Figure 5:
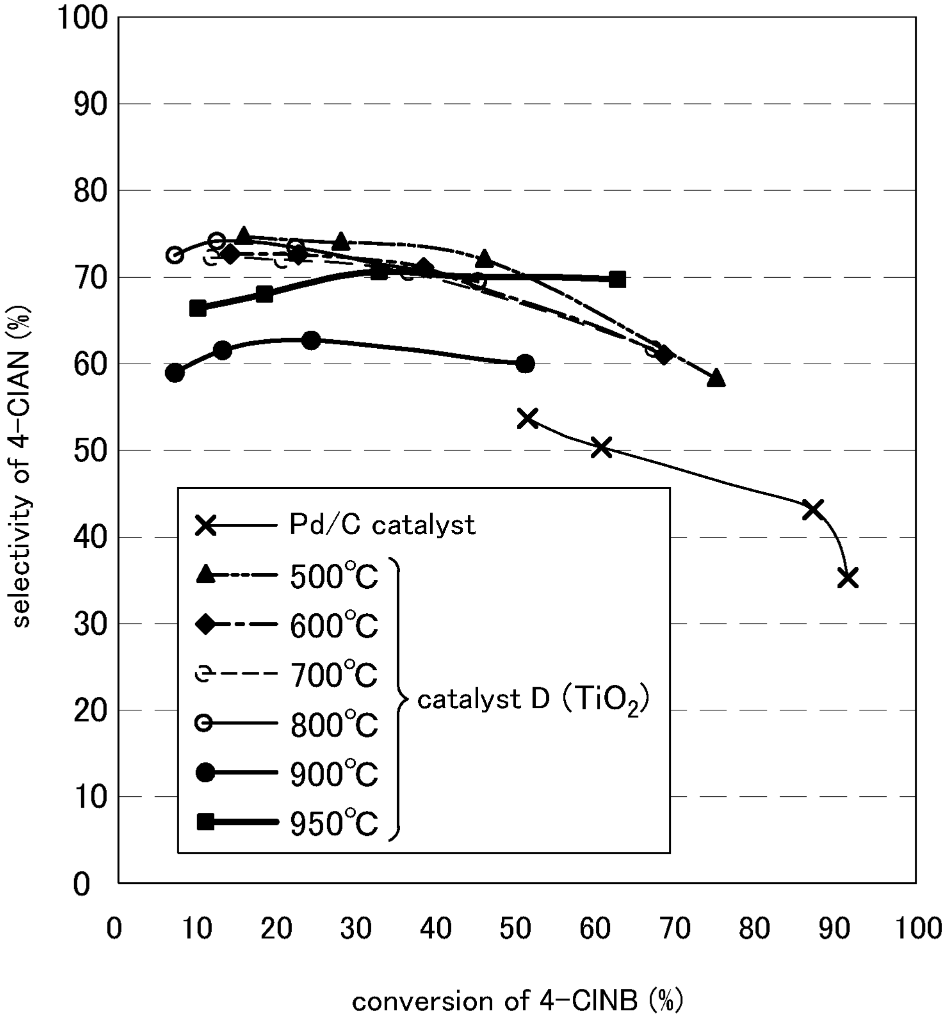
FIG. 5 is a graph (for the catalyst D) showing the relationship between the conversion of 4-CINB and the selectivity of 4-CIAN in the hydrogenation reaction.

FIGS. 4 and 5 are graphs showing the influence of the calcination temperatures (500° C., 600° ° C., 700° ° C., 800° C., 900° ° C., and 950° C.) of the carrier on the action (reaction characteristics) of the catalyst using the carrier containing titania. FIG. 4 shows, for the catalyst D at each calcination temperature of the carrier, the relationship between the conversion of 4-CINB as a liquid raw material and the selectivity of the nitroso compound (more specifically, 4-chloronitrosobenzene) in the hydrogenation reaction. FIG. 5 shows, for the catalyst D at each calcination temperature of the carrier that is the same as in FIG. 4, the relationship between the conversion of 4-CINB as a liquid raw material and the selectivity of 4-CIAN in the hydrogenation reaction.

In FIG. 4, in a case where the calcination temperature of the carrier for the catalyst D is 500° C., 600° ° C., and 700° C., the production of the nitroso compound is hardly confirmed (the selectivity of the nitroso compound is almost zero). By contrast, in a case where the carrier is calcined at a higher temperature (800° C. or higher), the production of the nitroso compound is confirmed. In particular, in a case where the calcination temperature of the carrier is 900° C. and 950° C. (900° ° C. or higher), the production of the nitroso compound is significant, and the selectivity of the nitroso compound for the catalyst D is equal to or higher than the selectivity of the nitroso compound for the Pd/C catalyst.

In FIG. 5, it is confirmed that the selectivity of 4-CIAN for the catalyst D tends to be higher than the selectivity of 4-CIAN for the Pd/C catalyst at any calcination temperature of the carrier.

Figure 6:
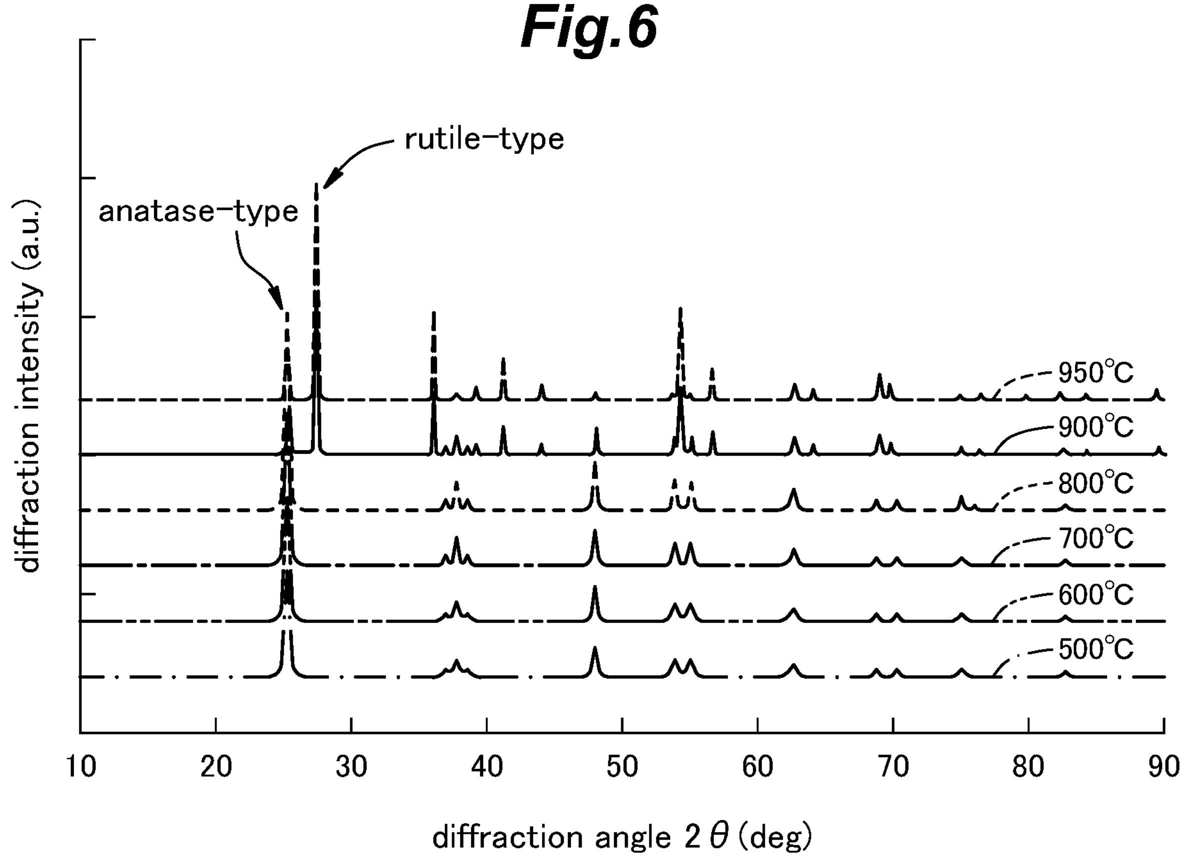
FIG. 6 is a graph (for the catalyst D) showing a diffraction pattern of an X-ray based on an X-ray diffraction method (XRD)

FIG. 6 is a graph showing a diffraction pattern of an X-ray based on an X-ray diffraction method (XRD) for the carrier of the catalyst D at the same calcination temperatures of the carrier as in FIGS. 4-5. As an X-ray diffraction device, a fully automatic multi-purpose horizontal X-ray analyzer (Smart Lab X-RAY DIFFRACTOMETER) manufactured by Rigaku Corporation was used. Further, quantitative analysis in the X-ray diffraction method was conducted by an RIR (Reference Intensity Ratio) method.

A peak (which appeared in the vicinity of a diffraction angle $2\theta=25.3°$ in a case where a CuK$\alpha$ ray was used as an X-ray source) corresponding to a {101} face of the anatase-type crystal phase indicating the presence of titania was detected in the diffraction pattern of the X-ray shown in FIG. 6. By contrast, at the calcination temperatures (800° C., 900° C., and 950° C.) of the carrier at which the nitroso compound was produced, a peak (which appeared in the vicinity of a diffraction angle $2\theta=27.4°$ in a case where a CuK$\alpha$ ray was used as an X-ray source) corresponding to a {110} face of a rutile-type crystal phase was detected in addition to the peak of the anatase-type. At the calcination temperatures 900° C. and 950° C. of the carrier at which the production of the nitroso compound was significant, the peak of the anatase-type was decreased, while the peak intensity caused by the rutile-type was remarkably high. Accordingly, it is confirmed that there is a correlation between the proportion of presence of the rutile-type crystal phase and the production behavior of the nitroso compound. In other words, in the catalyst containing titania, it is possible to suppress the production of the nitroso compound by increasing the ratio of the anatase-type crystal phase as a crystal phase.

Table 1 shows the percentage of each of the crystal phases (the anatase-type and the rutile-type) calculated based on the RIR method from the data of the X-ray diffraction at each of the calcination temperatures (500° C., 600° C., 700° C., 800° ° C., 900° C., and 950° C.) of the carrier of the catalyst D.

TABLE 1

| number | calcination temperature | percentage of crystal phase (%) anatase-type | rutile-type |
|---|---|---|---|
| 1 | 950 °C | 7.5 | 92.5 |
| 2 | 900 °C | 38 | 62 |
| 3 | 800 °C | 96.4 | 3.6 |
| 4 | 700 °C | 100 | 0 |

TABLE 1-continued

| number | calcination temperature | percentage of crystal phase (%) anatase-type | rutile-type |
|---|---|---|---|
| 5 | 600 °C | 100 | 0 |
| 6 | 500 °C | 100 | 0 |

Regarding the catalyst D, considering the selectivity of 4-CIAN and the selectivity of the nitroso compound shown in each of FIGS. 4 and 5 and the percentage of the anatase-type crystal phase shown in Table 1, it is confirmed that in a case where the percentage of the anatase-type crystal phase of the carrier containing titania is 38% or more, the yield of 4-CIAN (target product) is improved while suppressing the production of the nitroso compound as compared with the Pd/C catalyst. By setting the calcination temperature of the carrier containing titania to 900° C. or lower, the percentage of the anatase-type can be 38% or more.

Figure 7:
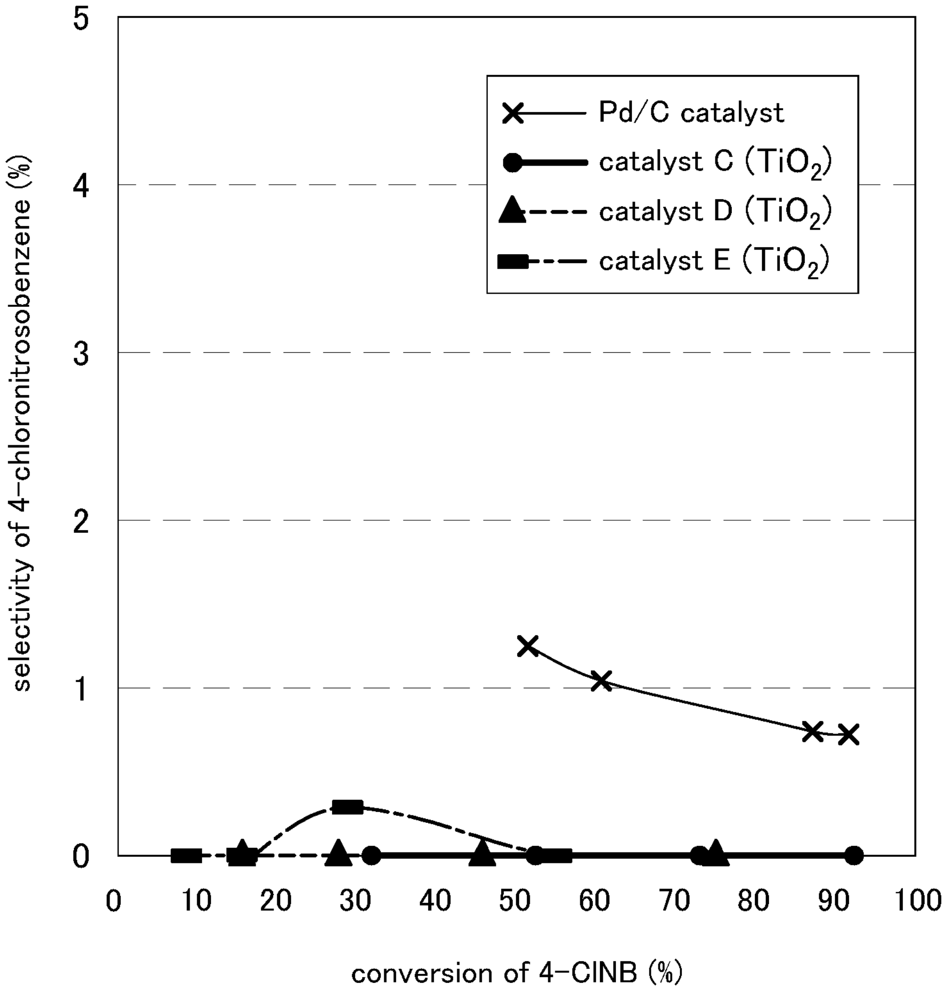
FIG. 7 is a graph (for the catalyst C, the catalyst D, and a catalyst E) showing the influence of the average pore diameter of a carrier on the action of a catalyst using a carrier containing titania.
Figure 8:
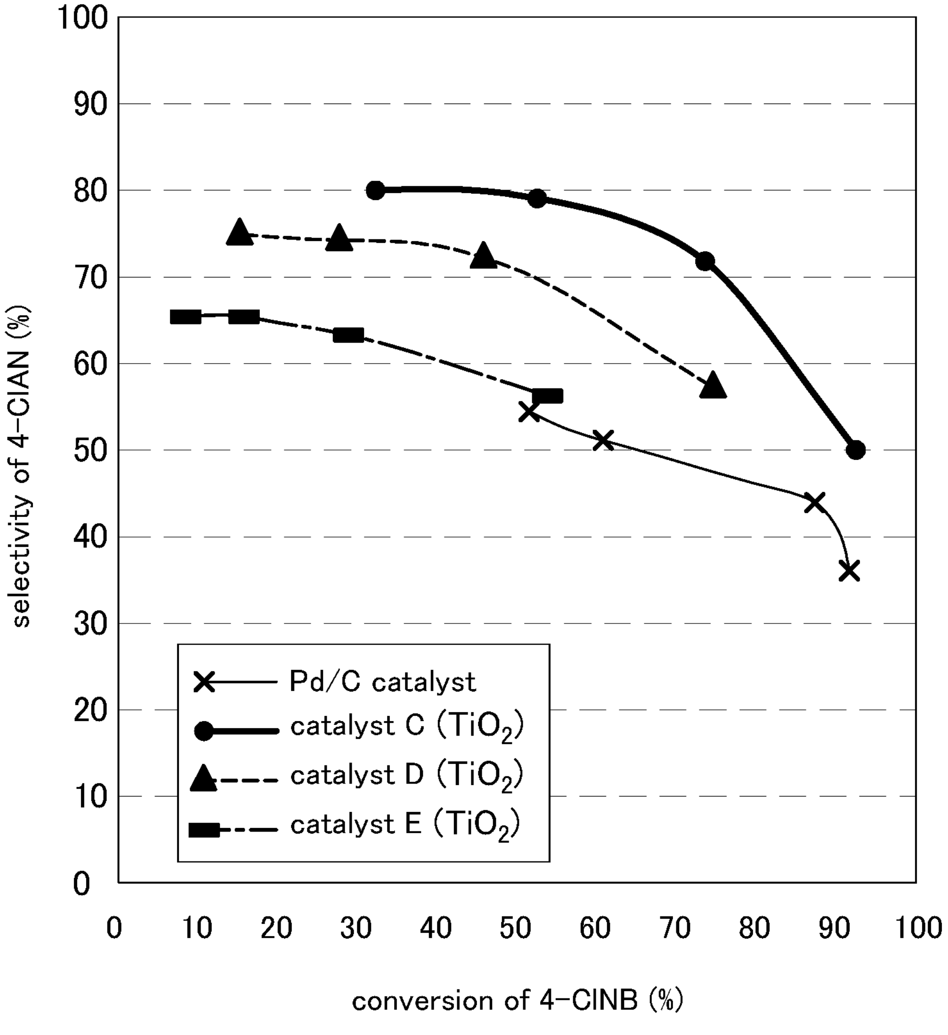
FIG. 8 is a graph (for the catalyst C, the catalyst D, and the catalyst E) showing the influence of the average pore diameter of the carrier on the action of the catalyst using the carrier containing titania.

FIGS. 7 and 8 are graphs showing the influence of the average pore diameter of the carrier on the action of the catalyst using the carrier containing titania. FIG. 7 shows the relationship between the conversion of 4-CINB as a liquid raw material and the selectivity of the nitroso compound (more specifically, 4-chloronitrosobenzene) in the hydrogenation reaction for the catalyst C, the catalyst D, the catalyst E, and the Pd/C catalyst (comparative catalyst). FIG. 8 shows the relationship between the conversion of 4-CINB as a liquid raw material and the selectivity of 4-CIAN in the hydrogenation reaction for the same catalysts as in FIG. 7.

Table 2 shows the average pore diameter of the carrier used in each of the catalyst C, the catalyst D, and the catalyst E. Each average pore diameter was measured based on mercury porosimetry. Further, as a pore distribution measuring device, "Micromeritics Automatic Mercury Porosimeter Autopore IV 9500" manufactured by Shimadzu Corporation was used.

TABLE 2

| catalyst | average pore diameter (4 V/A) (nm) | substrate length (nm) | quotient (average pore diameter/substrate length) (—) |
|---|---|---|---|
| C($TiO_2$) | 7.3 | 0.65 | 11.2 |
| D($TiO_2$) | 18.1 | 0.65 | 27.8 |
| E($TiO_2$) | 50.7 | 0.65 | 78 |

In FIG. 7, it is confirmed that the selectivity of the nitroso compound for all of the catalyst C, the catalyst D, and the catalyst E is lower than the selectivity of the nitroso compound for the Pd/C catalyst in a case where the conversion of 4-CINB is a similar value. In particular, in a case where the catalyst C and the catalyst D having a smaller average pore diameter are used, the nitroso compound is hardly produced.

In FIG. 8, it is confirmed that the selectivity of 4-CIAN for the catalyst C, the catalyst D, and the catalyst E tends to be higher than the selectivity of 4-CIAN for the Pd/C catalyst, in a case where the conversion of 4-CINB is a similar value.

Regarding the catalyst C, the catalyst D, and the catalyst E using the carrier containing titania, considering the selectivity of 4-CIAN and the selectivity of the nitroso compound shown in each of FIGS. 7 and 8 and the average pore diameter of the carrier shown in Table 2, it is confirmed that in a case where the average pore diameter of the carrier containing titania is approximately 50 nm or less, the yield of 4-CIAN (target product) is improved while suppressing the production of the nitroso compound as compared with the Pd/C catalyst. Further, it is confirmed that setting the average pore diameter to approximately 18 nm or less like the catalysts C and D is more preferable from the viewpoint of suppressing the production of the nitroso compound and improving the yield of 4-CIAN (target product). Further, it is confirmed that setting the average pore diameter to approximately 7 nm or less like the catalyst C is more preferable from the viewpoint of suppressing the production of the nitroso compound and improving the yield of 4-CIAN (target product). Further, as shown in Table 2, the average pore diameter of the carrier containing titania is preferably 78 times or less of the longitudinal molecular length (substrate length) of 4-CINB. Accordingly, it is possible to stably improve the yield of 4-CIAN as a target product while effectively suppressing the production of the nitroso compound. Further, the average pore diameter of the carrier containing titania is more preferably 28 times or less of the substrate length, and more preferably, 11 times or less thereof.

Figure 9:
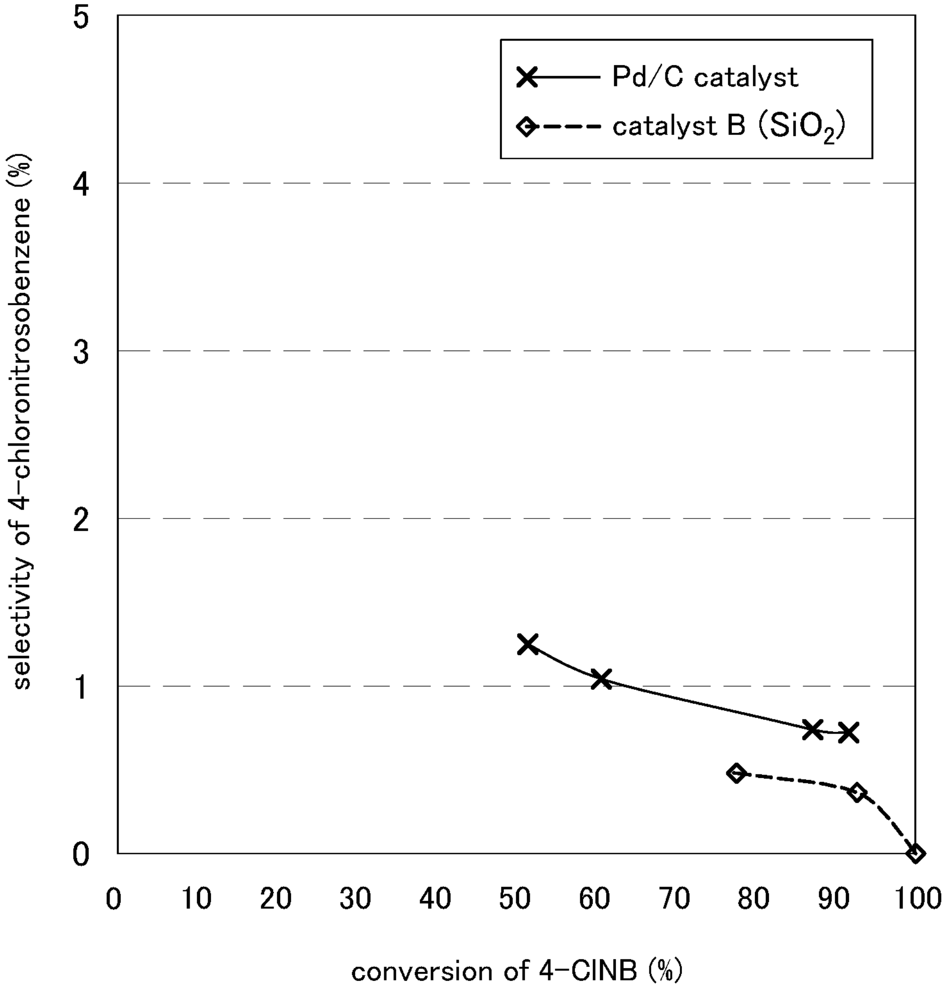
FIG. 9 is a graph (for a catalyst B) showing the influence of the average pore diameter of a carrier on the action of a catalyst using a carrier containing silica.
Figure 10:
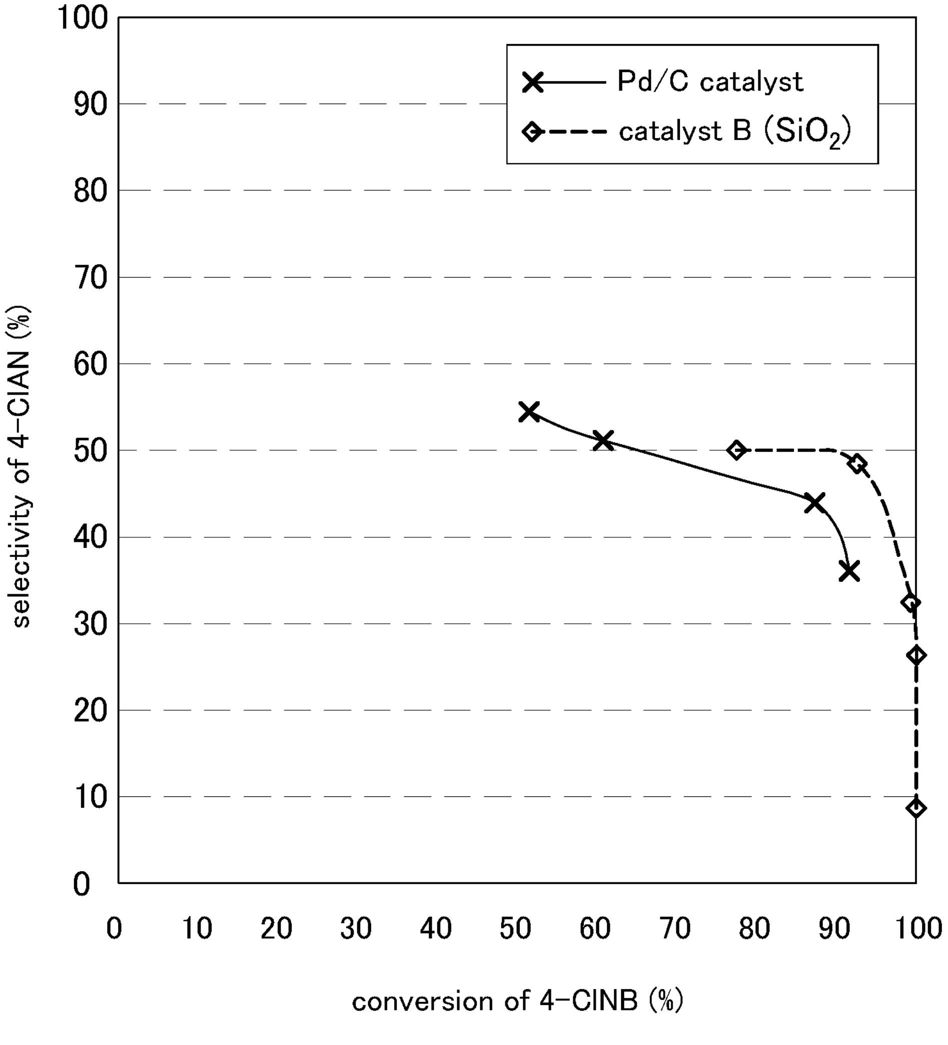
FIG. 10 is a graph (for the catalyst B) showing the influence of the average pore diameter of the carrier on the action of the catalyst using the carrier containing silica.

FIGS. 9 and 10 are graphs showing the influence of the average pore diameter of the carrier on the action of the catalyst using the carrier containing silica. FIG. 9 shows the relationship between the conversion of 4-CINB as a liquid raw material and the selectivity of the nitroso compound (more specifically, 4-chloronitrosobenzene) in the hydrogenation reaction for the catalyst B and the Pd/C catalyst (comparative catalyst). FIG. 10 shows the relationship between the conversion of 4-CINB as a liquid raw material and the selectivity of 4-CIAN in the hydrogenation reaction for the same catalysts as in FIG. 9.

The average pore diameter of the carrier of the catalyst B measured based on mercury porosimetry like the abovementioned Table 2 is 48.8 nm. Further, the average pore diameter of the carrier of the catalyst B is 75 times of the longitudinal molecular length (substrate length) of 4-CINB (average pore diameter/substrate length=75). The longitudinal molecular length of 4-CINB was calculated by Gaussian of a general-purpose quantum chemical calculation program. Accordingly, the average pore diameter of the carrier containing silica is preferably 75 times or less of the longitudinal molecular length (substrate length) of 4-CINB.

In FIG. 9, it is confirmed that the selectivity of the nitroso compound for the catalyst B tends to be lower than the selectivity of the nitroso compound for the Pd/C catalyst in a case where the conversion of 4-CINB is a similar value.

In FIG. 10, it is confirmed that the selectivity of 4-CIAN for the catalyst B tends to be higher than the selectivity of 4-CIAN for the Pd/C catalyst in a case where the conversion of 4-CINB is a similar value.

Regarding the catalyst B using the carrier containing silica, considering the selectivity of 4-CIAN and the selectivity of the nitroso compound shown in each of FIGS. 9 and 10 and the average pore diameter of the carrier thereof, in a case where the average pore diameter of the carrier containing silica is approximately 50 nm or less, there is a possibility of improving the yield of 4-CIAN (target product) while suppressing the production of the nitroso compound as compared with the Pd/C catalyst, like the abovementioned catalyst using the carrier containing titanium. Further, in a case where the quotient of the average pore diameter of the carrier of the catalyst B divided by the longitudinal molecular length (substrate length) of 4-CINB is 75 or less, there is a possibility of improving the yield of 4-CIAN (target product) while suppressing the production of the nitroso compound as compared with the Pd/C catalyst.

The present invention has been described above based on specific embodiments, but these embodiments are merely examples, and the present invention is not limited by these embodiments. Not all the components of the hydrogenation catalyst and the manufacturing method of the hydrogenated organic compound using the hydrogenation catalyst shown in the above-mentioned embodiments are essential, and at least those skilled in the art can select the components as appropriate within the scope of the present invention.

Glossary of Terms

1: flow-type organic synthesis system
2: flow-type fixed bed reactor
3: catalyst layer
4: electric furnace
11: liquid raw material tank
12: liquid raw material pump
13: preheater/precooler
21: heat exchanger
25: main drum
41: product recovery drum

The invention claimed is:

1. A hydrogenation catalyst configured to catalyze hydrogenation of an aromatic halonitro compound in a flow reaction for performing a gas/liquid/solid three-phase reaction, the hydrogenation catalyst comprising:

a carrier containing titania, the carrier having an average pore diameter of 50 nm or less; and palladium supported on the carrier;

wherein the average pore diameter is 78 times or less of a longitudinal molecular length of the aromatic halonitro compound.

2. A flow organic synthesis system configured to cause a gas/liquid/solid three-phase reaction by using:

a fixed catalyst including the hydrogenation catalyst according to claim 1;

hydrogen as a gas raw material; and the aromatic halonitro compound as a liquid raw material.

3. A manufacturing method of a hydrogenated organic compound, the method comprising:

hydrogenating the aromatic halonitro compound by using the hydrogenation catalyst according to claim 1.

* * * * *